United States Patent [19]

Kruse-Mueller et al.

[11] Patent Number: 6,027,885
[45] Date of Patent: Feb. 22, 2000

[54] METHOD FOR ELECTROCHEMILUMINESCENT LABELING OF NUCLEIC ACID, USE IN DETECTION, AND COMPOSITIONS THEREFOR

[75] Inventors: Cornelia Kruse-Mueller, Edewecht; Sibylle Berner, Starnberg; Cortina Kaletta, Munich, all of Germany

[73] Assignee: Roche Diagnostics GmbH, Mannheim, Germany

[21] Appl. No.: 08/771,256

[22] Filed: Dec. 20, 1996

Related U.S. Application Data

[62] Division of application No. 08/257,778, Jun. 9, 1994, Pat. No. 5,639,609.

[30] Foreign Application Priority Data

| Jun. 9, 1993 | [DE] | Germany | 43 19 151 |
| Nov. 16, 1993 | [DE] | Germany | 43 39 086 |
| Dec. 28, 1993 | [DE] | Germany | 43 44 742 |

[51] Int. Cl.[7] .................................................. C12Q 1/68
[52] U.S. Cl. ...................... 435/6; 435/91.1; 435/91.5; 436/501; 536/22.1; 536/25.3; 536/25.32; 935/77; 935/78
[58] Field of Search ................ 435/6, 810, 91.1, 435/91.5; 436/501; 536/22.1, 23.1, 24.1, 24, 37.33, 25.3, 25.32; 935/77, 78

[56] References Cited

U.S. PATENT DOCUMENTS

| 4,828,979 | 5/1989 | Klevan et al. | 435/6 |
| 5,210,015 | 5/1993 | Gelfand et al. | 435/6 |
| 5,487,972 | 1/1996 | Gelfand et al. | 435/6 |

FOREIGN PATENT DOCUMENTS

| 0 079 139 | 5/1983 | European Pat. Off. . |
| 0 192 168 | 8/1986 | European Pat. Off. . |
| 0 329 822 B1 | 8/1989 | European Pat. Off. . |
| 0 340 605 | 11/1989 | European Pat. Off. . |
| 0 201 184 B1 | 12/1992 | European Pat. Off. . |
| 0 566 050 | 10/1993 | European Pat. Off. . |
| WO 92/06216 | 4/1992 | WIPO . |

OTHER PUBLICATIONS

"Enzymatic synthesis of biotin-labeled polynucleotides: Novel nucleic acid affinity probes" Biochemistry: Langer et al, Proc. Natl. Acad. Sci USA 78 (1981 pp. 6634–6637.

Iribarren et al, *Proc. Natl. Acad. Sci. USA* 87, 7747–7751 (1990).

Holland et al, *Proc. Natl. Acad. Sci. USA* 88, 7276–7280 (1991).

*Primary Examiner*—Ardin H. Marschel
*Attorney, Agent, or Firm*—Nikaido Marmelstein Murray & Oram, LLP

[57] ABSTRACT

Method for immobilizing nucleic acids by hybridizing the nucleic acid with a capture probe. The capture probe is protected against enzymatic extension and/or enzymatic degradation of the formed hybrid.

9 Claims, 13 Drawing Sheets

I  II  III  IV  V  VI  VII  VIII  IX  X  XI  XII

XIII  XIV  XV  XVI  XVII  XVIII  IXX  XX  XXI  XXII

METHOD FOR ELECTROCHEMILUMINESCENT LABELING OF NUCLEIC ACID, USE IN DETECTION, AND COMPOSITIONS THEREFOR

This is a division of application Ser. No. 08/257,778 filed Jun. 9, 1994; now U.S. Pat. No. 5,639,609.

Subject matter of the invention are methods for immobilizing nucleic acids, methods for detecting nucleic acids making use of this immobilization, reagents for implementing this method and corresponding reagent kits.

When detecting nucleic acids, a distinction is made between homogeneous and heterogeneous assay methods. In homogeneous methods, the detection probes and the nucleic acids to be detected are assayed in solution, whereas in heterogeneous methods the nucleic acid to be detected is immobilized. This immobilization is achieved either by directly attaching the nucleic acid to a solid phase via covalent binding or by coupling the nucleic acid to one partner of an affinity pair while binding the remaining partner of this pair to a solid phase.

Coupling can also be achieved by immobilizing the nucleic acid by hybridizing it to a so-called capture probe which is bound to a solid phase and at least partly complementary to the nucleic acid to be detected. The capture probe is or can be bound to a solid phase in any desired manner. An advantage of heterogeneous methods is that labelled reagent components can be easily separated from the nucleic acid to be detected.

Examples for methods where the nucleic acids to be detected are immobilized via capture probes can be found in EP-A-0 079 139 which describes direct binding and in EP-A-0 192 168 which describes binding via an affinity pair. A characteristic feature of the assay methods described therein is the hybridization of the nucleic acid to be detected with a capture probe. After removing excess detection probe, the so formed hybrid is then detected at the solid phases via a labelling group of the capture probe.

With the introduction of target-specific amplification processes to nucleic diagnostics, it was possible to produce large amounts of otherwise rarely occurring nucleic acids. A method of this kind where a digoxigenin label is incorporated into the amplified nucleic acid, is described in WO 92/06216.

PCT/US 92/01735 discloses a method for preparing 2'-substituted nucleic acids and their resistance to degradation by restriction enzymes. Further, it is also known that when nucleic acids are sequenced, 3'-deoxynucleotides truncate chains and inhibit the extension of nucleic acids in 3'-direction.

It is an object of the present invention to provide a particularly simple and efficient method of immobilization.

Subject matter of the invention is a method for immobilizing nucleic acids by hybridizing the nucleic acid with a capture probe whereby the capture probe is protected against enzymatic extension and/or enzymatic break-down of the formed DNA/RNA-hybrid.

Other subject matters of the invention are a method for detecting a nucleic acid making use of the immobilization according to this method and reagents suitable for this purpose.

A capture probe is a nucleic acid which can hybridize with another nucleic acid or which is or can be immobilized. Immobilization is a procedure whereby a nucleic acid is bound to a solid phase. This can either be a direct binding (covalent binding of the capture probe to the surface of the solid phase) or an indirect binding (ionic, adsorptive, or biospecific binding). In the invention, preferred nucleic acid are nucleic acids which are labelled with a partner of a biospecific pair while allowing immobilization. Biospecific pairs are such combinations as antigen/antibody, hapten/antibody, vitamin/receptor, hormone/receptor, and sugar/lectin. Preferred combinations are biotin/avidin, biotin/streptavidin, or hapten/antibody. So labelled nucleic acids can be prepared, for example, by means of chemical oligonucleotide synthesis using correspondingly labelled active mononucleoside derivatives or by means of enzymatic synthesis via incorporation of correspondingly labelled mononucleoside triphosphates or by chemically modifying fully synthesized nucleic acids.

Enzymatic extension is a process that occurs in living cells or in fluids deriving from such cells which still contain active enzymes. The process is triggered by enzymes such as polymerases which extend nucleic acids. These extension reactions may significantly interfere with the determination of nucleic acids, particularly when corresponding enzymes have been added to the sample to carry out the amplification process.

In order to suppress this extension reaction, the invention proposes to protect the capture probe against extension. This can be achieved by attaching chemical residues which inhibit steric access of extension enzymes to the 3'- or 5'-end. As these residues sometimes inhibit or even completely prevent hybridization of the capture probe with the immobilizing nucleic acid, it is preferred to replace the hydroxyl group at which the extension would take place by an inactive group.

Such groups include, for example, hydrogen or C1–C3-alkyl groups, with hydrogen being preferred. At their ends, the so obtained capture probes, therefore, contain a 3'- or 5'-deoxyribonucleoside residue or a 2',3'- or 2',5'-dideoxyribonucleoside residue. The 3'-end of the capture probe is the preferred end to be protected.

Enzymatic break-down is also a common phenomenon in biological sample liquids. Such a break-down is caused by endo- or exonucleases such as DNAses or RNAses. This also includes restriction enzymes. If, for example, RNA is to be used as a nucleic acid to be immobilized, this RNA would be subject to degradation by RNAseH as soon as a hybrid consisting of DNA as the capture probe and the RNA is formed. This means immobilization by means of unmodified DNA capture probes is very inefficient or even impossible. The present invention attempts to eliminate this by modifying the capture probe with the result that the above mentioned enzymes no longer recognize the hybrid of capture probe and nucleic acid to be detected as substrate.

The modification of sugar residues of the capture probes, e.g., at the 2'-position, has proven to be quite efficient. A particularly preferred combination for the immobilization of RNA in the presence of RNAseH is one where the 2'-hydroxyl group of deoxyribonucleotides is replaced by O-alkyl or O-alkylene groups. Particularly preferred combinations are described in WO 91/15499.

Surprisingly, it is possible to protect nucleic acids effectively against enzymatic break-down of the RNA/DNA-hybrid and enzymatic extension by simultaneously employing the described measures. This modifications are selected such that their effects and actions do not negatively affect one another.

Capture probes include oligo or polynucleotides which can also be further modified. However, this modification must exclude the possibility that hybridization is rendered impossible by base-pairing with the nucleic acid to be immobilized.

Immobilized capture probes are nucleic acids which are bound to a solid phase. The binding can be achieved by forming covalent links or biospecifically via two partners forming a biospecific link (e.g. hapten/antibody, vitamin/receptor, preferably biotin/streptavidin) whereby one of the partners is bound to the capture probe while the other is bound to the solid phase.

Capture probes which can be immobilized are nucleic acids which are not yet bound to a solid phase, but which can be turned into the above mentioned immobilized capture probes. To achieve this, the immobilized capture probes contain either a residue capable of chemically reacting with the solid phase (e.g. residues which can be photoactivated) or a partner of a biospecific binding.

Possible solid phases include cuvettes, microtiterplates or particles (e.g. plastic-coated magnetic beads).

To achieve an immobilization of the nucleic acids in accordance with the invention, the capture probe is brought into contact with a sample that contains the nucleic acid to be immobilized. Hybridization is carried out under conditions which depend on the length of the nucleic acid used and the capture probe. The expert is capable of determining these conditions in a few experiments, e.g. by determining the melting temperature. Generally, however, these conditions will not differ from those for nucleic acids having the same (unmodified) nucleotide sequence as the capture probe.

If the capture probe that is used is an already immobilized nucleic acid, hybridization of the capture probe with nucleic acid occurs simultaneously with the immobilization of the nucleic acid. If desire, the hybrid formed at the solid phase can now be separated from the liquid which contained the nucleic acid. Subsequently, the solid-phase bound hybrid can be washed and is available for further reactions, if necessary.

If the capture probe is one that can be immobilized, the hybrid-containing liquid is brought into contact with a solid phase capable of immobilizing the capture probe. To achieve this, the solid phase preferably contains a binding partner of the group used to immobilize the capture probe. As is the case with immobilized capture probes, further processing steps may follow.

The nucleic acid to be immobilized can be one of any desired kind and of any desired origin. These may be nucleic acids occurring in natural samples, e.g. body fluids or cultured samples, but also samples obtained by processing natural samples. They can, hence, be modified or unmodified. The modifications can relate to the sequence, length and/or the chemical structure of the nucleic acids. In a preferred case, the nucleic acids are copies of a nucleic acid or a nucleic acid sequence that was originally contained in the sample. Moreover, preferred copies are amplification products resulting from an in-vitro amplification of a part of the original nucleic acid. Particularly preferred amplification products are those formed as templates by enzymatic extension of the nucleic acid at the original nucleic acid. Examples for such in-vitro amplifications are PCR, LCR or promoter-controlled amplifications.

In another preferred embodiment, the nucleic acids are modified by incorporating detectable groups. This incorporation can be implemented via enzymatic or chemical reactions. Enzymatic reactions are particularly preferred as they occur during amplification as described above. In this case, it has proven to be particularly expedient to use detectable modified monocucleoside triphosphates for the extension. In preferred manner, all non-incorporated detectable groups are then separated. If the nucleic acid to be immobilized is modified such that it can be detected, it can be detected at the solid phase in a known manner once it is immobilized. The detection step may, hence, follow the immobilization process. Another subject matter of the invention is a method for detection nucleic acid using the immobilization process of the invention followed by the detection of the immobilized hybrids. In a particularly preferred manner, the detectable groups are determined at the immobilized nucleic acid.

Detectable groups are directly or indirectly detectable groups. Directly detectable groups include, for example, radioactive (hu 32P), colored, or fluorescent groups or metal atoms. Indirectly detectable groups include, for example, immunological or enzymatically effective compounds such as antibodies, antigens, haptens, or enzymes, or enzymatically active partial enzymes. They are detected in a subsequent reaction or sequence of reactions. Haptens are particularly preferred as they generally perform well with labelled nucleoside triphosphates as substrates of polymerases and as the subsequent reaction with a labelled antibody to the hapten or the haptenized nucleoside can be readily implemented. Such nucleoside triphosphates are, for example, bromine-nucleoside triphosphate or digoxigenin, digoxin- or fluorescein-coupled nucleoside triphosphates. The steroids described in EP-A-0 324 474 and their detection have proven to be particularly suitable. For details on their incorporation refer to EP-A-0 324 474.

In a first embodiment of the method of the invention, the nucleic acid to be detected is detected via a detection probe which is hybridized to it. This detection probe has a nucleotide sequence which can hybridize to a segment of the nucleic acid to be detected, said segment being different from the one to which the capture probe hybridizes. The result is a so-called sandwich hybrid consisting of capture probe, nucleic acid to be detected and detection probe. The hybridization sequence of these three nucleic acids can principally be freely selected. In a preferred manner, sandwich formation occurs essentially simultaneously. In a particularly preferred embodiment of the sandwich test, the capture probe is added to the sample containing the nucleic acid to be detected. Subsequently, the nucleic acid to be detected or part thereof are amplified and then the hybrids formed under hybridization conditions are detected with the aid of the detection probe. As is the case with the capture probe, it is also possible to correspondingly protect the detection probe against enzymatic extension/break-down and to add it before or during amplification.

In a preferred embodiment, the nucleic acid to be detected is amplified in the presence of a capture probe immobilized to a solid phase while detectable, labelled nucleotides, especially mononucleotides, are enzymatically incorporated. After a possible separation of excess mononucleotides the nucleic acid immobilized to the solid phase is determined via the amount of incorporated detectable nucleotides. A particularly preferred amplification for the invention is the method described in EP-A-0 329 822. It is a particular advantage of the method of this specification to modify the capture such that the RNA (transcripts) to be immobilized are protected against degradation by the hybrid of capture probe and RNA.

When an immobilizable capture probe is used, the invention proposes two embodiments. If a first embodiment, the nucleic acid to be detected is amplified in the presence of the immobilizable capture probe and detectably labelled mononucleotides. All known amplification methods can be employed. A preferred method is the polymerase chain reaction (EP-B-0 201 184) with thermal cycles allowing denaturing between the cycles; the amplification reaction can be carried out in any desired vessel. Subsequently, the reaction mixture is transferred into a vessel to the solid phase of which the immobilizable capture probe can be immobilized. It is preferred to separate excess mononucleotides and to use the label at the solid phase as a measure for the presence of the nucleic acid to be detected.

In a second, preferred embodiment, the amplification reaction already occurs in a vessel where the immobilizable nucleic acid can be bound to the inner wall. It is an advantage that a transfer of the amplification mixture into another vessel is no longer required. If thermocyclically controlled amplification reactions are used, e.g. PCR or LCR, the invention proposes to use thermostable vessel having corresponding coatings.

Provided the reaction vessel is already suitable for detecting hybrids and when direct labels are used, the reaction can be controlled from the start of the amplification until the end of the detection without adding reagents.

Currently known methods have the disadvantage that after the amplification procedure, the reaction mixture had to be exposed to the environment to add the probes (contamination). If the probes are added together with the amplification reagents, the procedure advantageously requires fewer pipetting steps and, secondly, the reaction vessel must not be opened again after amplification and addition of reagents (e.g. capture probe). This characteristic feature is particularly advantageous for methods with direct labels which do not require the addition of reagents to detect the label. In such cases, e.g. electrochemiluminescence labels, no reagent is added from the start of the amplification until the measurement of the analyte-dependent signal. The addition of regents is, however, possible at any time.

Another subject matter of the invention are nucleic acids which are modified to be protected against both enzymatic break-down of nucleic acids in hybrids of the nucleic acid and complementary nucleic acids as well as enzymatic extension and, further, their use as capture probes to immobilize nucleic acids. In a preferred manner, these nucleic acids are modified at positions of the nucleobase, especially at the functional amino groups, which are capable of establishing hydrogen bridges to complementary nucleic acids. They are not modified with respect to the natural nucleobases.

Another subject matter of the invention is a reagent kit comprising a first container A with an enzyme for extending nucleic acids and a second container B with a capture probe in accordance with the invention.

This or other containers preferably contain all other reagents necessary for immobilization and amplification or detection of nucleic acids. Such reagents are buffers, mononucleoside triphosphates, labelling reagents and the like.

A particularly preferred container B features either a detectable detection probe which is also modified in accordance with the invention or detectable mononucleoside triphosphates. Moreover, container A can contain a nucleic acid especially an enzyme which degrades RNA in a RNA/DNA-hybrid.

Subject matter are also special electrochemiluminescence-labelled mononucleoside triphosphates.

Groups which have electrochemiluminescent properties are known. They are hereinafter referred to as electrochemiluminescene group E. Particularly preferred electrochemiluminescent components of E are coordination complexes K with an atomic weight of more than 500 g/mol, preferably 550 to 2000 g/mol. Preferred metal ions are ions of the VIIb and VIIIb subgroups of the periodic table, particularly Ru, Os, Re, with ruthenium being particularly preferred.

Suitable ligands of the metal ion in the coordination complex are in particular organic ligands or groups as described in WO 92/10267 or EP-A-0 340 605.

Suitable organic ligands are hydrocarbons which contains atoms which acts as electron donors for the corresponding metal atom, e.g. nitrogen, oxygen, or sulfur. The electron donors are suitably disposed in a geometric arrangement so as to allow complex formation with the metal ion. In case of ruthenium, the bipyridil residues are preferred ligands.

Moreover, via one of the ligands, the complex is bound to a mononucleoside triphosphate. In a preferred manner, a spacer group A is disposed between the coordination complex and the atoms of the nucleoside triphosphate. The spacer group preferably is an atomic chain consisting of 3, particularly 5 to 15, more particularly 4 to 10 atoms with additional groups being bound to the side of the chain, if necessary. The chain of atoms preferably contains a hydrocarbon chain which can be interrupted by heteroatoms, e.g. —O—(oxygen) or an $NR^2$-group where N is nitrogen and $R^2$ hydrogen or a $C_1$–$C_6$ alkyl group. The chain of atoms preferably contains once the component —($CR^3_2$—$CR^3_2$—O) wherein $R^3$ is hydrogen or a $C_1$–$C_6$ alkyl group. The spacer group has a preferred molecular weight of less than 1000 g/mol.

Preferably, the electrochemiluminescene group E is covalently bound to an atom of the nucleobase N of the mononucleotide.

Preferred sites for the linking are C5, C6, C4 or N4 for pyrimidines and C8 or N6 for purines and C7 for deazapurines.

Preferred mononucleoside triphosphates are those of formula I

P—Z—B—E  (I)

wherein

P is a triphosphate group or a triphosphate analog group

Z is a sugar or sugar analog group

B is a nucleobase or nucleobase analog group and

E is an electrochemiluminescene group.

Triphosphate, sugar, and nucleobase are the groups contained in naturally occurring mononucleoside triphosphates. Analog groups are those groups which are obtained by replacing one or several atoms, but yet do not essentially inhibit the property of the compounds of formula I, namely the incorporation in nucleic acids.

Triphosphate analogs are groups, for example, where one or several oxygen atoms are replaced by sulfur atoms. Sugar analogs are groups where the endocyclic oxygen atom is replaced by the —$CR^4_2$—group, wherein $R^4$ is hydrogen or a $C_1$–$C_6$ alkyl group. Nucleobase analogs are, for example, deazapurines, preferably 7-deazapurines.

Preferred mononucleotide triphosphates are compounds of the formula Ia

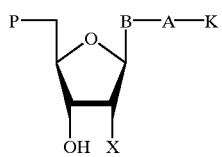

wherein

X is hydrogen or the $OR^1$-group $R^1$ is a $C_1$–$C_6$ alkylene group of hydrogen B is a purine, deazapurine or a pyrimidine group A is a spacer group and K is an electrochemiluminescent coordination complex.

and the alkali and earth alkali salts thereof.

Experience has surprisingly shown that even groups as large as the described metal complexes do not essentially interfere with the incorporation of mononucleoside triphosphates labelled therewith by means of enzymes catalyzing the incorporation of mononucleoside triphosphates in nucleic acids. The incorporated amount of labelled mononucleoside triphosphates is sufficient for the detection of nucleic acid labelled therewith by means of electrochemiluminescence. The method of the invention exhibits a higher degree of sensitivity in comparison to prior art methods using electrochemiluminescene.

It is particularly surprising to see the very high dynamic measurement range, i.e. the ratio of the greatest quantifiable amount of nucleic acids to be determined at a given concentration of mononucleoside triphosphates to the lowest quantifiable amount. This ratio can exceed values of $10^7$.

The mononucleoside triphosphates can be incorporated in different ways.

One way is the extension of oligonucleotides, so called primers, which are hybridized to the nucleic acid to be detected. A segment of a nucleic acid is attached to the 3'-end of the primer in a reaction that is catalyzed by a polymerase, preferably DNA-polymerase. This segment is essentially complementary to the corresponding segment of the nucleic acid to be detected. This reaction can occur cyclically using the formed extension products while amplifying a segment of the nucleic acid present. Such a method is described in EP-A-0 201 184.

Another possibility is the replication or transcription of nucleic acids which contain an origin of replication or a promotor. In this case, the nucleic acids are composed solely of mononucleotides without primer extension. Examples are known from WO 91/03573 or WO 91/02818.

During the incorporation, at least one type of mononucleotides ((d)ATP, (d)CTP, (d)GTP, or dTTP/(d)UTP) is partially or completely replaced in the reaction mixture by the electrochemiluminescent mononucleoside triphosphates. In a preferred manner 10 to 50% of one type of mononucleoside triphosphates (e.g. dUTP) are replaced by the labelled analog (e.g. ruthenium-complex-labelled dUTP). A preferred concentration of the labelled mononucleoside triphosphate ranges between 20 and 70 µM, particularly preferred is a range between 25 and 40 µM. All other conditions for the incorporation reaction do not essentially differ from those mentioned in the above mentioned documents.

Depending on their structure, the electrochemiluminescene-labelled mononucleoside triphosphates can be produced in different manners.

If the group is to be attached to the nucleobase, an amino group of the natural bases can be reacted with an electrophilic group, e.g. an activated ester group of the spacer group.

It has proven to be particularly expedient to react those mononucleoside triphosphates with such a reactive electrochemiluminescent compound which already possesses at one atom of the base a spacer group with an amino group. An example are the mononucleoside triphosphates containing substituted in position 5 with an alkyl amino group. (Proc. Acad. Sci. USA 78, 6633–37 (1991).

An electrochemiluminescent compound having a reactive group can be purchased, for example, from the IGEN company. The amide is formed under conditions similar to those applying to the regular formation of amides from activated esters and amines.

Figure 13:
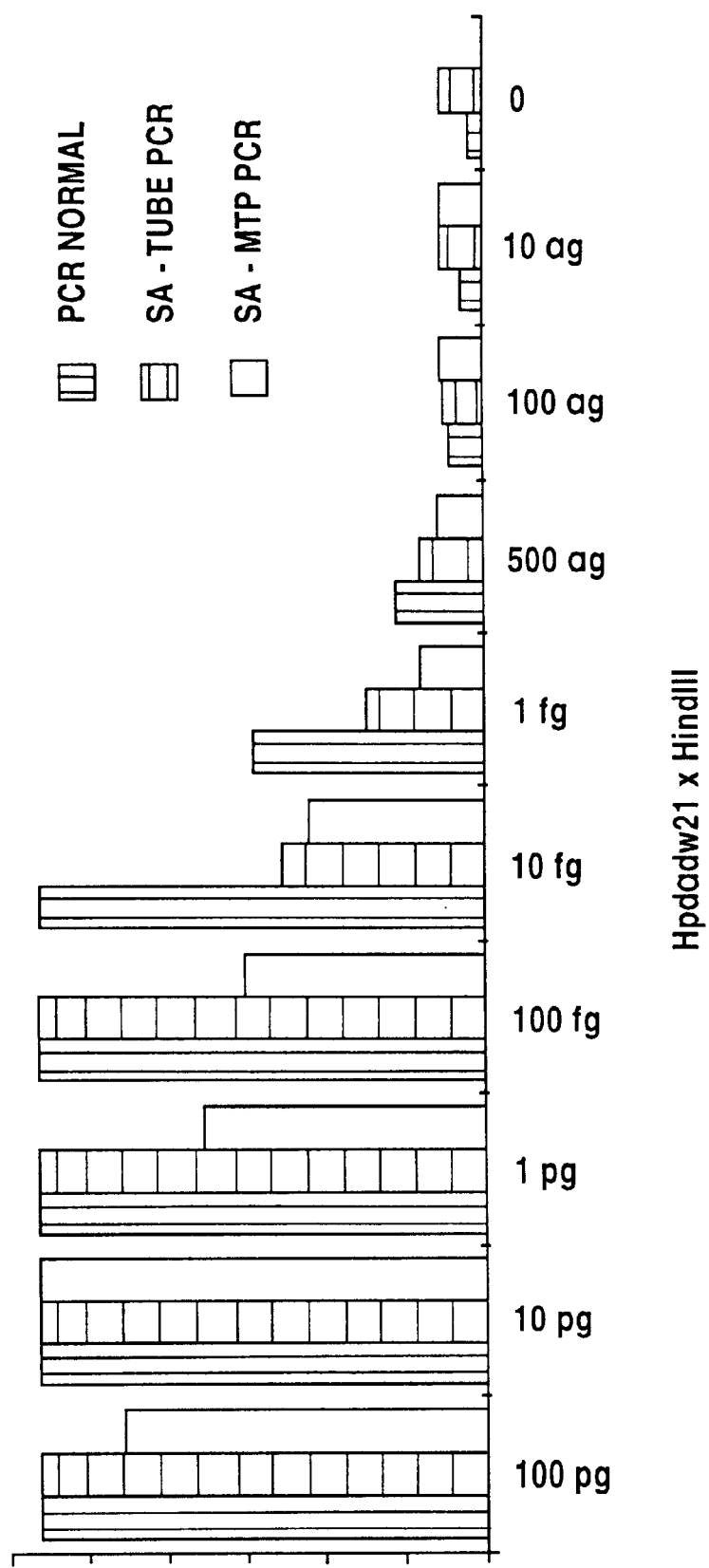

FIG. 13 is a graph comparing the different embodiments of the invention. The bar with the vertical lines stands for an embodiment where a second vessel was used to specifically bind the capture probe whereas the bars with the cross lines stand for an example where amplification and wall binding were carried out in one single vessel. The dotted bars relate to an embodiment where the reaction mixture for detecting the color in solution which developed during the enzymatic reaction is transferred in a detection vessel.

Each of the references and patent documents cited in the present application are hereby incorporated by reference into the present application. Specifically, these documents include EP-A-0 079 139; EP-A-0 192 168; WO 92/06216; PCT/US92/01735; WO 91/15499; EP-A-0 324 474; EP-A-0 329 822; EP-B-0 201 184; WO 92/10267; EP-A-0 340 605; WO 91/03573; WO 91/02818; EP-A-0 200 362; EP-A-0 269 092; WO 90/08197; EP-B-0331 127; Schmitz, G. G., et al. (1990) Anal. Biochem. 192,222; Inoue, H., et al. (1987) FEBS Lett. 215, 327–330; Iribarren, A. M., et al., (1990) PNAS 87, 7747–7751; Maniatis et al., Molecular Cloning: A Laboratory Manual, CSH, 194–195, 1982; Kievits, T. et al. (1991), J. of Virol Methods, 273–286; Leland et al., (1990), J. Electrochem. Soc., 137, 3127–33; Langer et al., (1981) Proc. Natl. Acad SCI, USA, 78, 6633–37, 1981; Bergstrom et al. (1977), J. Carbohydr., Nucleosides, Nucleotides, 4:257; Ono et al. (1983), Nucl. Acids Res. 11:1747–1757; Kessler et al. (1980) "Nonradioactive labeling and Detection of Nucleic acids", Biol. Chem. Hoppe-Seyler 371:917–927; and Blackburn et al. (1991) Clin. Chem. 37:1534–1539.

The following examples are intended to further illustrate the invention:

EXAMPLE 1

Detection of HBV with Direct and Subsequent Use of a Capture Probe

Hpbadw21 in a concentration of 1 ng to 100 atg per reation mixture were used as a target for the polymerase chain reaction (PCR)(EP-A-0 200 362) The volume for the PCR mixture was 100 µl.

The mixture was composed as follows:

| | Final concentration |
|---|---|
| Primer 1 (SEQ. ID. NO. 1) | 200 nM |
| Primer 2 (SEQ. ID. NO. 2) | 200 nM |
| dATP (Boehringer Mannheim) | 200 µM |
| dCTP (Boehringer Mannheim) | 200 µM |
| dGTP (Boehringer Mannheim) | 200 µM |

-continued

| Final concentration | |
|---|---|
| dTTP (Boehringer Mannheim) | 175 µM |
| dig-11-dUTP (Boehringer Mannheim GmbH, Best. Nr 1093088) | 25 µM |
| PCR-Puffer | 1 X |
| Taq-DNA-Polymerase (Perkin Elmer) | 2.5 U |
| PCR-Mix | 99 µl |
| Sample | 1 µl |
| Volume | 100 µl |

10 X PCR Puffer: 100 mM Tris/HCl, 500 mM KCl, 15 mM MgCl$_2$, 1 mg/ml gelatine, pH 9.0
Primer 1: Oligodeoxynucleotide, 18 mer, d (GGAGTGTGGATTCGCACT) (Pos. 2267–2284; EMBL, subtype adw, SEQ. ID. NO. 1)
Primer 2: Oligodeoxynucleotide, 18 mer, d (TGAGATCTTCTGCGACGC) (Pos. 2436c–2419c, EMBL, Subtype adw, SEQ. ID. NO. 2)
Hpbadw 21: cloned HBV-DNA; nucleotide 29–2606 (EMBL) of the HBV$_{adw}$-sequence cloned in pUCBM20 (Boehringer Mannheim) and linearized.
Biotinylated capture probe: d (AGCCTATAGACCACCAAATGCCCCTAT) 5'-biotinylated (SEQ. ID. NO. 3) Pos. 2290–2316; EMBL, subtype adw Ref.: Ono et al. (1983). Nucl. Acids Res. 11

The PCR mixtures were amplified in a Perkin Elmer Thermal Cycler under the following cycle conditions: 3'93° C.; (1'94° C., 1'50° C., 2'70° C.)×30; 5'95° C., 37° C.

The biotin-labelled probe was in a concentration of 100 ng per reaction mixture. During the PCR, the probe was block at its 3'-end with Bio-16-ddUTP (Boehringer Mannheim, Cat. No. 1427, 598) Ref.: Schmitz, G. G. et al. (1990) Anal biochem. 192, 222).

Streptavidin-coated microtiterplates were used for the detection (Boehringer Mannheim GmbH, EP-A-0 269 092).
1. Detection of PCR without probe followed by hybridization:

Following the amplification procedure, 40 ng of biotin-labelled capture probe were added to 20 µl of a PCR reaction mixture. This mixture was heat up to 95° C. for 5', then cooled on ice and for 15 min incubated at 37° C. Then, 180 µl hybridization buffer were added (50 mM phosphate buffer, 750 mM NaCl, 75 mM Na citrate, 0.05% BSA, pH 6.8); this mixture was then pipetted into the well of a streptavidin-coated (SA) microtiterplate and for 1 hour incubated at 37° C. After washing the mixture 3 times with 0.9% NaCl, 200 µl of conjugate buffer 100 mM TRIS×HCl, 0.9% NaCl, 1% BSA, pH 7.5 with 0.2 U/ml anti-digoxigenin-POD (Boehringer Mannheim) were added by pipetting and for 20 min incubated at 37° C. Once again washed 3 times, 200 µl ABTS® (1.9 mmol/l) were used for the detection and the absorbance was measured at Hg 405 nm.
2. Detection of the PCR with the probe being used directly during the PCR (as proposed by the invention)

The amplification was carried out in the presence of 100 ng of capture probe.

Following the amplification 180 µl hybridization buffer were added directly to 20 µl of a PCR reaction mixture and treated as described under 1.

Figure 1:
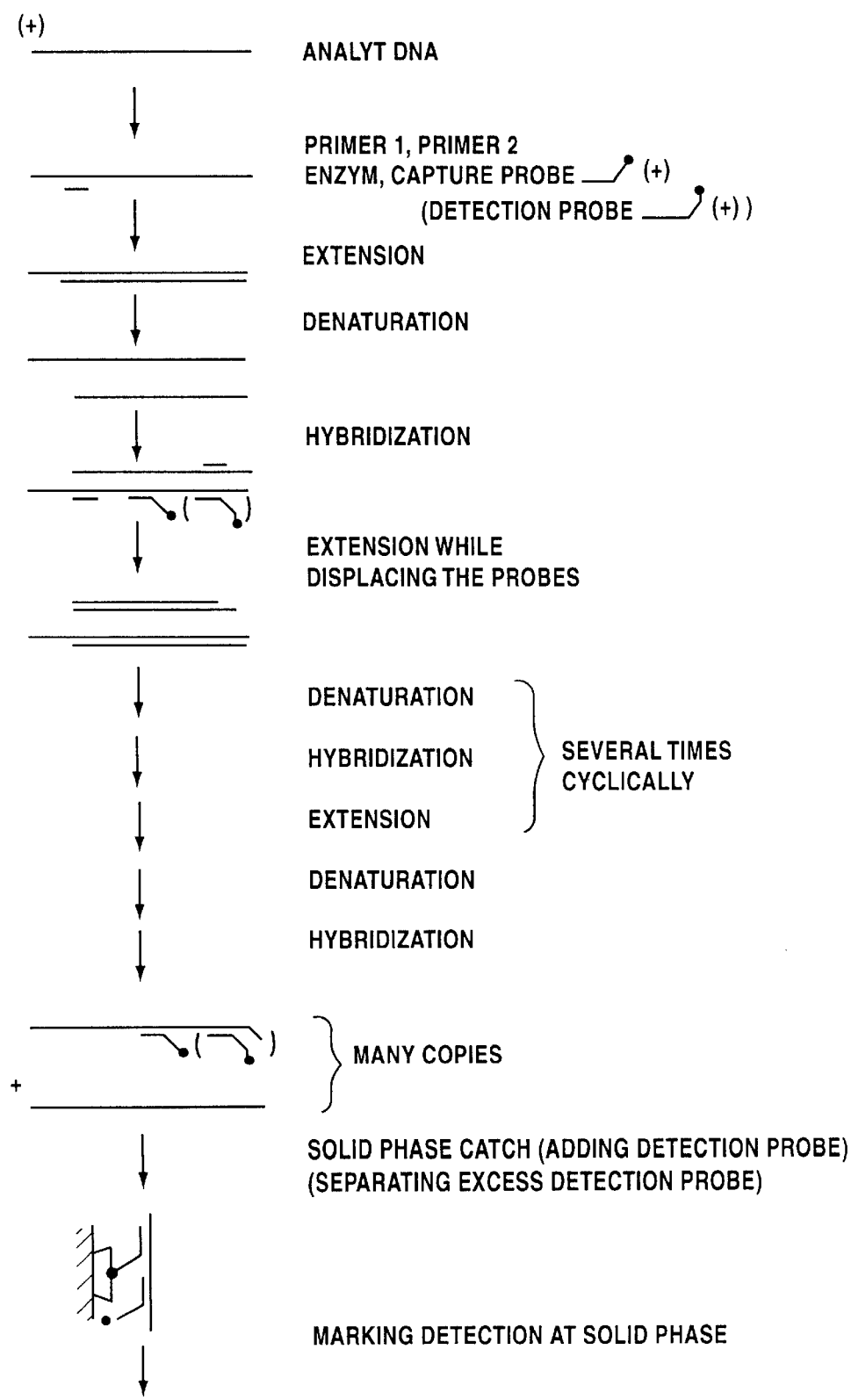
FIG. 1 is a diagram showing the detection method in accordance with the invention using PCR for the amplification.
Figure 2:
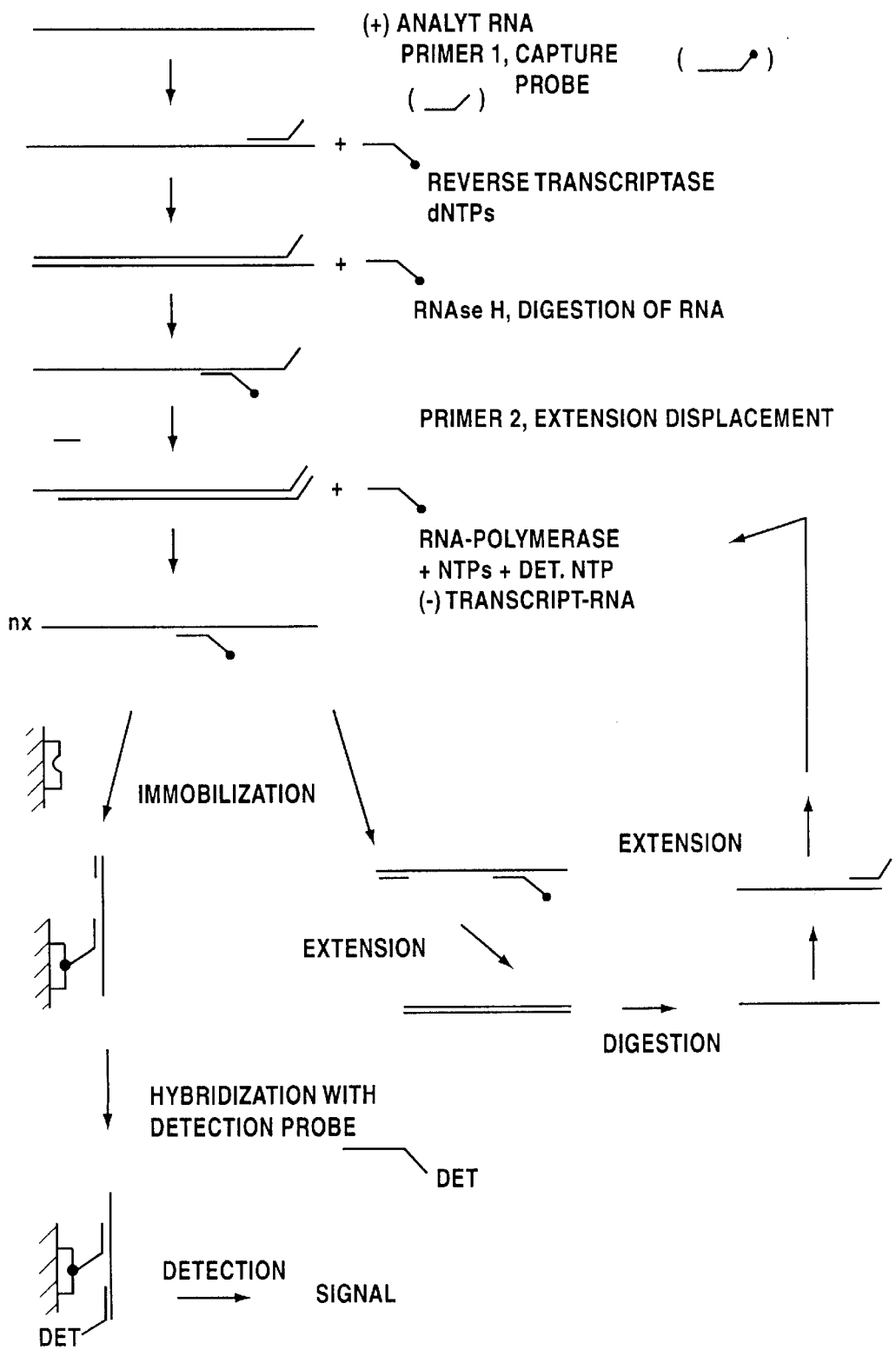
FIG. 2 is a diagram showing the detection method in accordance with the invention using NASBA for the amplification.
Figure 3:
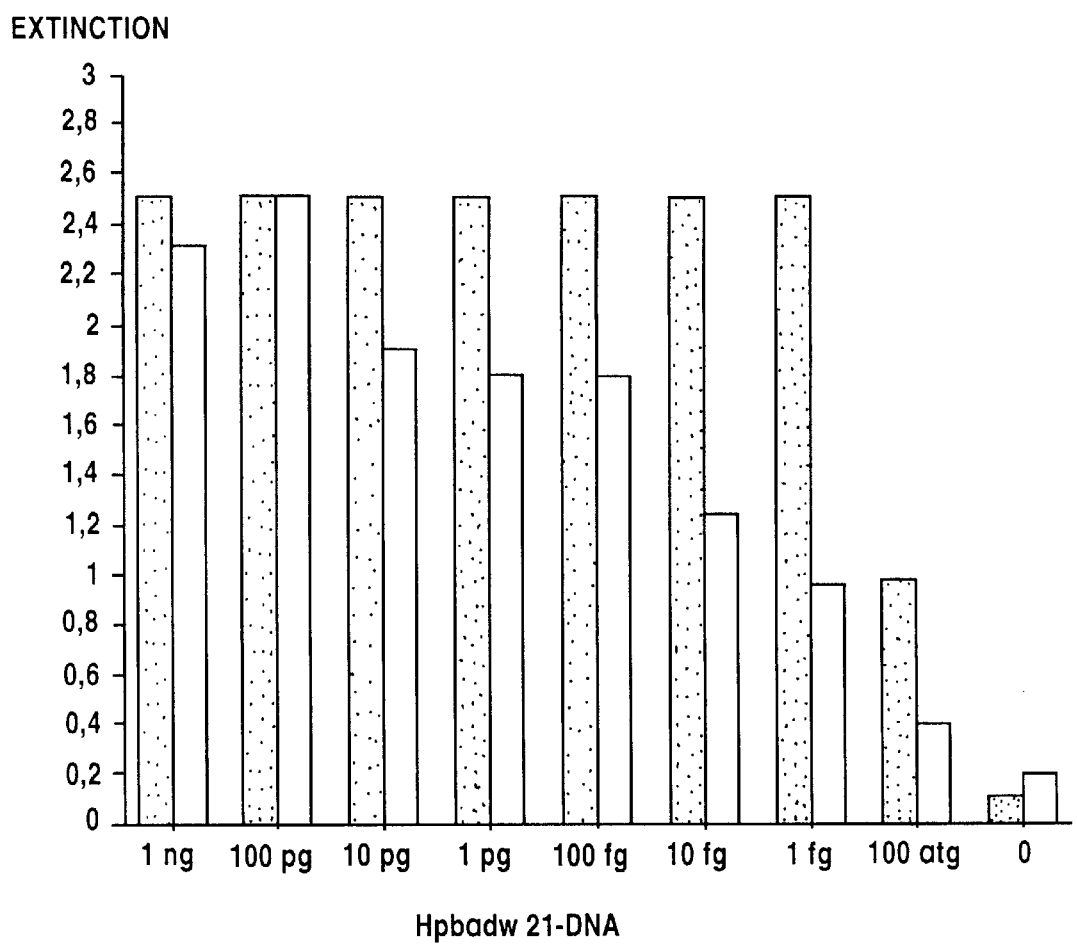
FIG. 3 is a graph showing the results of HpBadw21-DNA determinations in accordance with the invention (PCR with probe) as compared to PCR without probe (dark bars).

The results are shown in FIG. 3.

EXAMPLE 2

Promotor-Controlled Amplification With and Without Direct Use of a Probe (NASBA)

The analyte used was isolated chromosomal Listeria monocytogenes DNA (see WO 90/08197) in concentrations of 50 ng to 5 fg per reaction mixture. NASBA is described in EP-A-0 329 822.

The NASBA is preceded by a reaction to convert the double-stranded analyte DNA into single-stranded DNA using the T$_7$-RNA polymerase promotor sequence (PreNASBA). This is normally achieved by using Sequenase®. Principally, however, any DNA polymerase is suitable.

| 1 PreNASBA-(Prereaction) | Final concentration in the PreNASBA |
|---|---|
| 10 X NASBA-Buffer | 1 X |
| Primer 3 | 0.2 µM |
| dATP (Pharmacia) | 1 mM |
| dCTP (Pharmacia) | 1 mM |
| dGTP (Pharmacia) | 1 mM |
| dTTP (Pharmacia) | 1 mM |
| ATP (Pharmacia) | 2 mM |
| CTP (Pharmacia) | 2 mM |
| GTP (Pharmacia) | 2 mM |
| UTP (Pharmacia) | 2 mM |
| dig11-UTP (Boehringer Mannheim) Best. Nr. 1209256) | 10–20 µM |
| +Target DNA | |
| PreNASBA-Mix | 20 µl |

This mixture was heated up to 95° C. for 5 minutes and then cooled on ice.

It was adjusted to 10 mM dithiothreitol (DTT); then, 13 U T$_7$-DNA polymerase (Sequenase®, by United States Biochemicals) were added. The mixture was then incubated for 15 min at 37° C. and again heated up to 95° C. and again cooled on ice.

11A NABSA Amplification: Reaction Procedure 1
a. Composition of reaction mixture The volume used for the NASBA was 25 µl (23 µl NASBA-Mix+2 µl PreNASBA-Mix, from example 2, Part 1).

| Reagent | Final concentration in NASBA |
|---|---|
| 10 X NASBA-Buffer | 1 X |
| DTT | 10 mM |
| dATP | 1 mM |
| dCTP | 1 mM |
| dGTP | 1 mM |
| dTTP | 1 mM |
| ATP | 2 mM |
| CTP | 2 mM |
| GTP | 2 mM |
| UTP | 2 mM |
| dig UTP | 10–20 µM |
| RNase Inhibitor (by Boehringer Mannheim) | 0.48 U |
| T$_7$-RNA-Polymerase (by Boehringer Mannheim) | 80 U |
| AMV-RT (by Boehringer Mannheim) | 4 U |
| RNaseH (by Boehringer Mannheim) | 1 U |
| Primer 3 | 0.2 µM |
| Primer 4 | 0.2 µM |
| DMSO | 15% |
| | 23 µl |
| +Product from PreNASBA | 2 µl |
| | 25 µl |

10 x NASBA Puffer: 400 nM TRIS/HCl, 500 mM KCl, 120 mM MgCl$_2$, pH 8.5
Primer 3: d (AATTCTAATACGACTCACTATAGGGAGACGCGCTTTA-CCTGCTTCGGCGATT), SEQ. ID. NO. 4 PIII-Region (Pos. 35–56). The underlined portion is the T$_7$-RNA-Polymerase Promotor sequence.
Primer 4: d (GTAATCATCCGAAACCGCTCA), SEQ. ID. NO. 5 PIII-Region (Pos. 196c–216c)

The NASBA amplification was allowed to occur for 1.5–2 hours at 40° C.
b. Hybridization After the amplification, 200 ng of biotinylated probe were added to the NASBA mixture and heated up to 95° C. for 5 min and then cooled on ice. Then, the mixture was incubated for 30 min at 37° C.

Probe: d(CGTTTTACTTCTTGGACCG). SEQ ID. No. 6 at the 5'-end biotinylated with biotinamite (Applied Biosystems) PIII region (Pos. 162c–180c)

c. Detection in microtiterplates

195 µl hybridization buffer (50 mM phosphate buffer, 750 mM NaCl, 75 mM Na-citrate, 0.05% BSA, pH 6.8) were added to 5 µl of the hyridization mixture. The mixture was then pipetted into the well of a microtiterplate and incubated for another hour at 37° C. After washing three times with 0.9% NaCl solution, incubation was continued for 20 minutes with 200 µl 0.2 U/ml anti-digoxigenin-POD (Boehringer Mannheim) in conjugate buffer (100 mM TRIS-HCl, 0.9 NaCl, 1% BSA, pH 7.5) at 37° C. The mixture was washed again three times and then 200 µl ABTS® (Boehringer Mannheim) (1.9 mmol/l) were added and the absorbance was measured at Hg 405 nm.

11B NASBA Amplification: Reaction Procedure 2 a. Composition of reaction mixture

The composition of the NASBA reaction mixture corresponded to the one used in 11A. In addition, the capture probe was added directly during amplification in a concentration 140 ng per mixture.

A 2'-allylribooligonucleotide which was biotin-labelled (biotin amide by Applied Biosystems Inc.) at the 5'-end and blocked with a hydrophilic linker at its 3'-end was used for the direct employment of the capture probe during the NASBA reaction. A 2'-O-allyl-modified oligoribonucleotide was used as a probe as this "RNA strand" is not degraded by RNAseH in RNA/DNA hybrids (Ref.: Inoue, H. et al (1987) FEBS Lett. 215, 327–330). The 3'-end of the oligonucleotide was blocked to avoid a non-specific extension during the polymerase reaction.

sequence: 5'-biotin-CGU UUU ACU UCU UGG ACC -G-3'-block (SEQ ID. No. 7)

C=2'—O—allyl cytidine
G=2'—O—allyl guinosine
A=2'—O—allyl adenosine
U=2'—O—allyl uridine This capture probe was synthesized with 2'—O—allyl nucleoside phosphorus amidites by Boehringer Mannheim Biochemicals according to the protocol by Iribarren et al. (Ref.: Iribarren, A. M. et al. (1990) PNAS 87, 7747–7751) using an oligonucleotide synthesizer by Pharmacia (Gene Assembler)

b. Hybridization does not apply c. MTP detection

The procedure corresponded to the one used for Ic with 5 ml of NASBA mixture.

Figure 4:
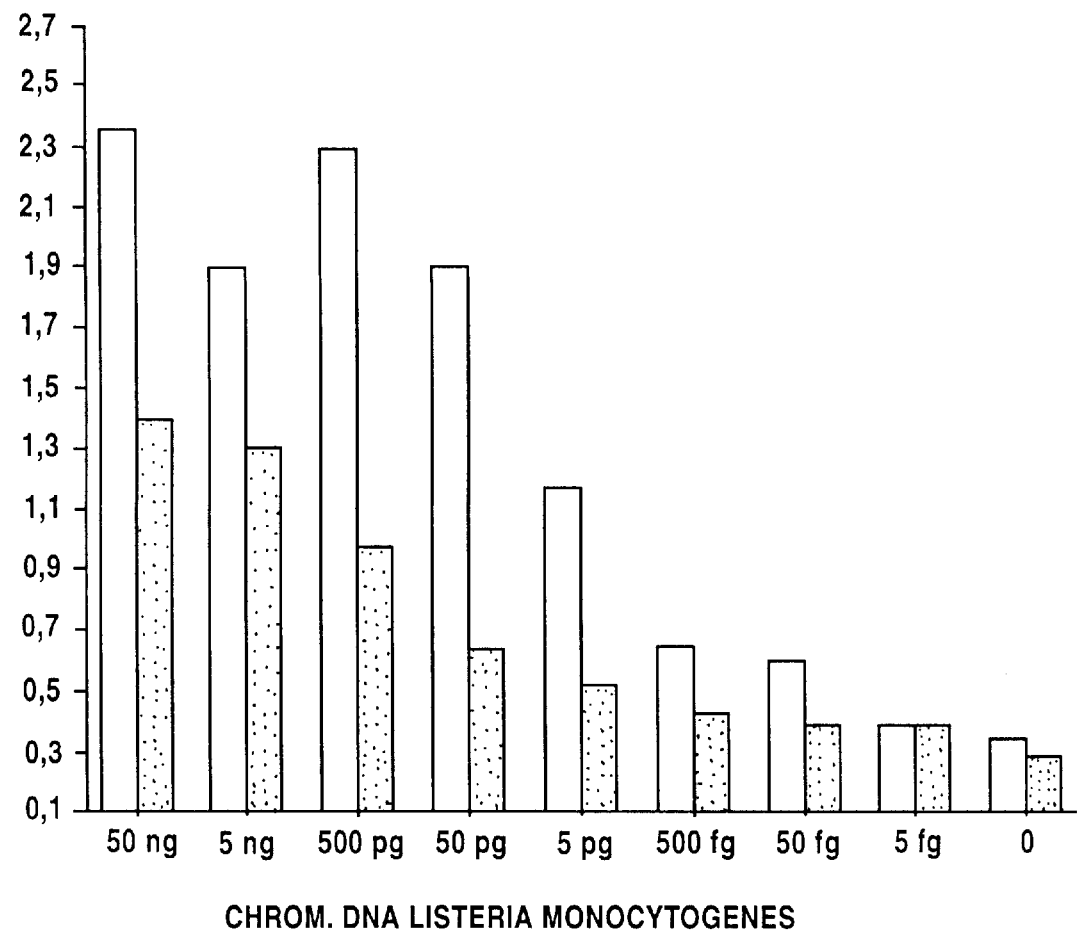
FIG. 4 is a similar graph for Listeria determinations using NASBA (with probe; dark bars).

The results are summarized in FIG. 4.

EXAMPLE 3

Detection of HIV-1 Using NASBA

In the following example, HIV-1 was detected with the aid of the NASBA amplification system (EP-A-0 329 822). NASBA was carried out in the presence of the biotin-labelled capture probe. The amplification product was detected directly via the incorporated label (ruthenium-labelled UTP).

The tests covered HIV-positive sera of patients with AIDS or ARC (AIDS related complex). The RNA was isolated after the Guanidinum Hot Phenol Method according to Maniatis et al. [Molecular Cloning: A laboratory manual (Cold Spring Harbor Lab., Cold Spring Harbor, N.Y. 194–195, 1982) and the RNA solution were stored at −70° C. in aliquots of 10 µl. Prior to the NASBA reactions, the RNA solution were diluted 1:10, 1:100, 1:1000, 1:10000 and 2 µl were used in the NASBA reaction.

For the NASBA reaction and the composition of the reaction mixture, refer to example 2 IIb: 30 µM ruthenium-labelled UTP (=Ru(bpyr)₃-AA-UTP) were used instead of digUTP (for details on the synthesis see example 4).

Primers and probe used:

OT 188: <u>AATTCTAATACGACTCACTATAGGG</u>CCTGGCTTTAATTTTACTGGTA
P1 (SEQ. ID. NO. 8)
OT 42: ACAGGAGCAGATGATACAGTATTAG
P2 (SEQ. ID. NO. 9)
OT 15: 5'-Bio-UGGAAGAAAUCUGUUGACUCAGAUUGGUUGC-block-3'
Sample (SEQ. ID. NO. 10)

The underlined portion of sequence OT 188 corresponds to the T₇-RNA-polymerase promotor.

Oligonucleotide OT 15 is again a 2'-O—allyl ribooligonucleotide blocked at its 3'-end (see example 2 IIB) and biotinylated at its 5'-end.

Ref.: Kievits, T. et al. (1991). *J. of Virol. Methods* 273–286.

Detection of the Amplification Products

After the reaction, 10 µg (2×10⁶ beads) magnetic beads (Dynabeads® M-280. Streptavidin, Dynal) in 20 µl phosphate buffer (62 mM Na-phosphate, 0.94 M NaCl, 94 mM Na-citrate, pH 7) were added to 5 µl of NASBA reaction mixture and incubated for 30 minutes at 37° C.

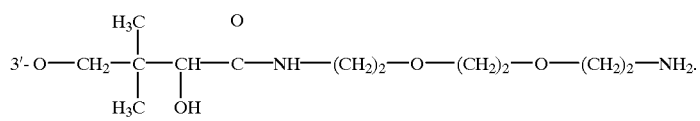

Subsequently, a magnet was used to collect the beads at the bottom of the sample cup. The were washed twice each time with 100 µl phosphate buffer. Then, the beads were suspended in 100 µl of said phosphate buffer and 250 µl ECL assay buffer (0.2 M KH₂PO₄, 0.05 M NaCl, 0.1 M tripropylamin, pH 7.5; Ref.: J. K. Leland et al. (1990). *J. Electrochem. Soc.* 137:3127–33) were added. The measurement was carried out on an ECL Analyser (Origen 1.0; Manufactured by Igen Inc.) with a photomultiplier voltage of 940 V. The measurement time was 2 seconds at a ramp of 2 V per second. The entire measuring cycle for each sample was 2 minutes.

Figure 5:
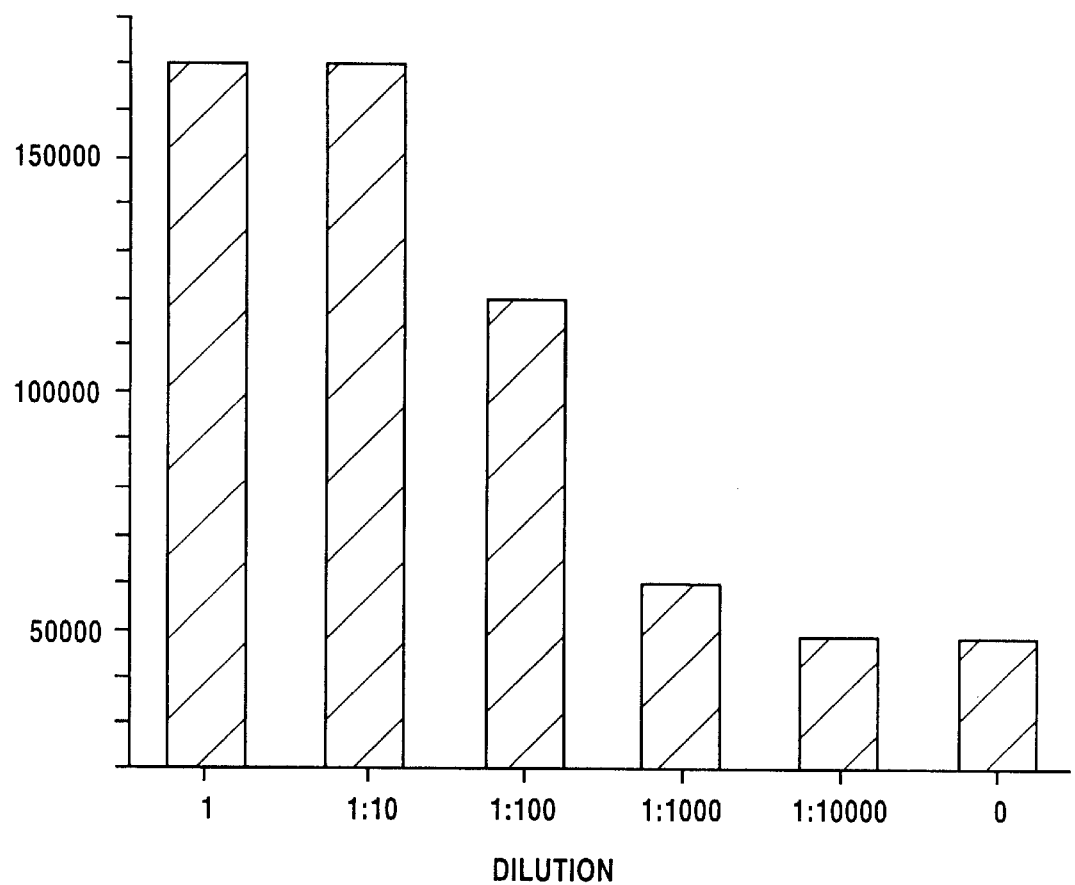
FIG. 5 shows the result of an HIV 1 determination using electrochemiluminescent labels in the presence of the capture probe with NASBA.
Figure 6:
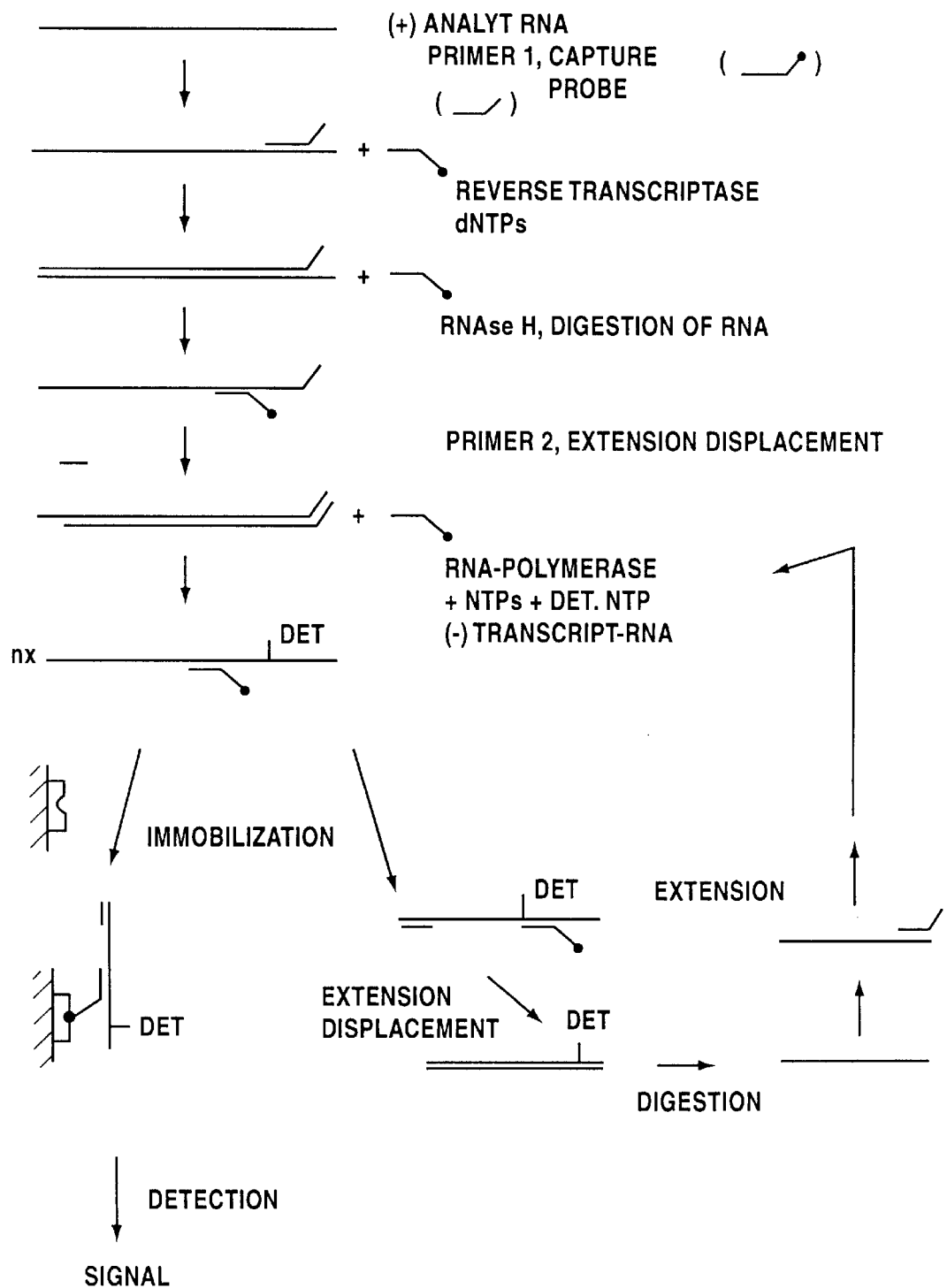
FIG. 6 is a reaction scheme for the amplification and detection of nucleic acids using NASBA where a digoxigenin-labelled mononucleoside is incorporated in the transcripts.

The result is summarized in FIG. 5.

EXAMPLE 4

Synthesis of Ru(bpyr)$_3$-AA-UTP

Origen® label (Igen Inc.)=[4-(N-succinimidyl-oxycarbonylpropyl)-4'-methyl-2,2'-bipyridine-bis(2,2'-bipyridine)]-ruthenium (II)-dihexaflurophosphate AA-UTP=5-(3-aminoallyl)-uridine triphosphate was prepared according to Langer et al. [Proc. Natl. Acad. Sci. USA. 78, 6633–37, 1981]

DMSO=dimethylsulfoxide 5.5 mg (0.01 mmol) AA-UTP (lithium salt) were dissolved in 2 ml 0.1 M sodium borate buffer (pH 8.5). To achieve this, a solution of 15.8 mg (0.015 mmol) of the Origen® label were added to 1.5 ml DMSO and stirred overnight at room temperature. Subsequently, the Ru(bpyr)$_3$-AA-UTP product was purified by means of ion exchange chromatography (Sephadex DEA, Cl form; gradient; 0—0, 4 M LiCl). Yield: 7 mg (46% of theoretical).

EXAMPLE 5

Synthesis of Ru(bpyr)$_3$-AA-dUTP and Ru(bpyr)$_3$-DADOO-dUTP 5-(3-aminoallyl)-dUTP (=AAdUTP) was prepared according to Langer et al. (1981). Proc. Natl. Acad. Sci. USA. 78:6633–37; DADOO-dUTP was obtained by reacting 5-mercury-dUTP with N-allyl-N'-(8-amino-3,5-dioxaoctyl)urea.

Figure 7:
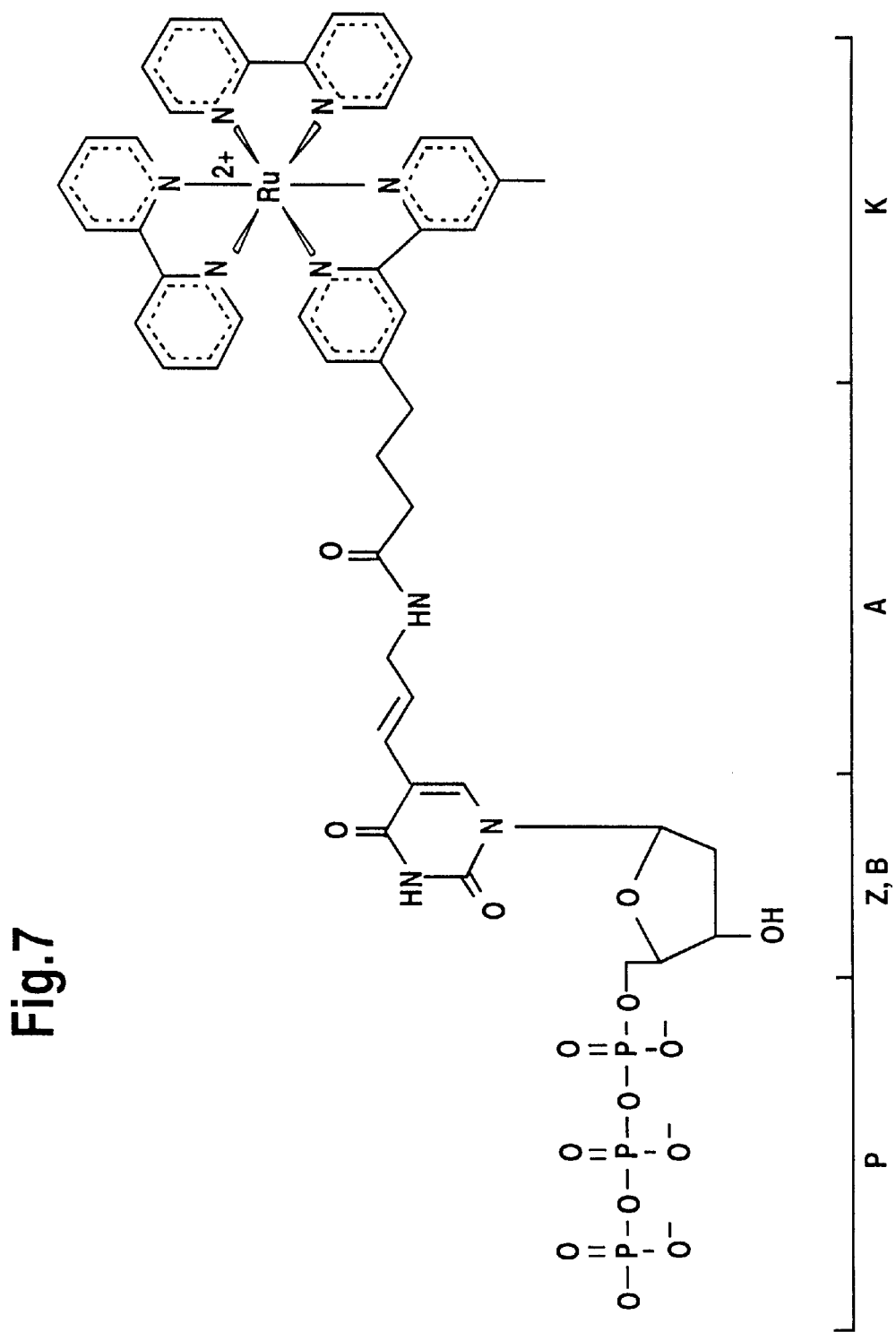
FIG. 7 shows the structure of Ru(bpyr)$_3$-AA-dUTP.

Synthesis of Ru(bpyr)$_3$-AA-dUTP (FIG. 7)

3.2 mg AAdUTP were dissolved in 0.1 M sodium borate buffer and stirred overnight at RT with a solution of 5.6 mg of the Origen® label in 560 μl DMSO.

The reaction was controlled via TLC and paper electrophoresis and the product was then purified by means of ion exchange chromatography.

Yield: 3.8 mg (48% of theoretical)

[M+H]$^+$: 1180.1

Figure 8:
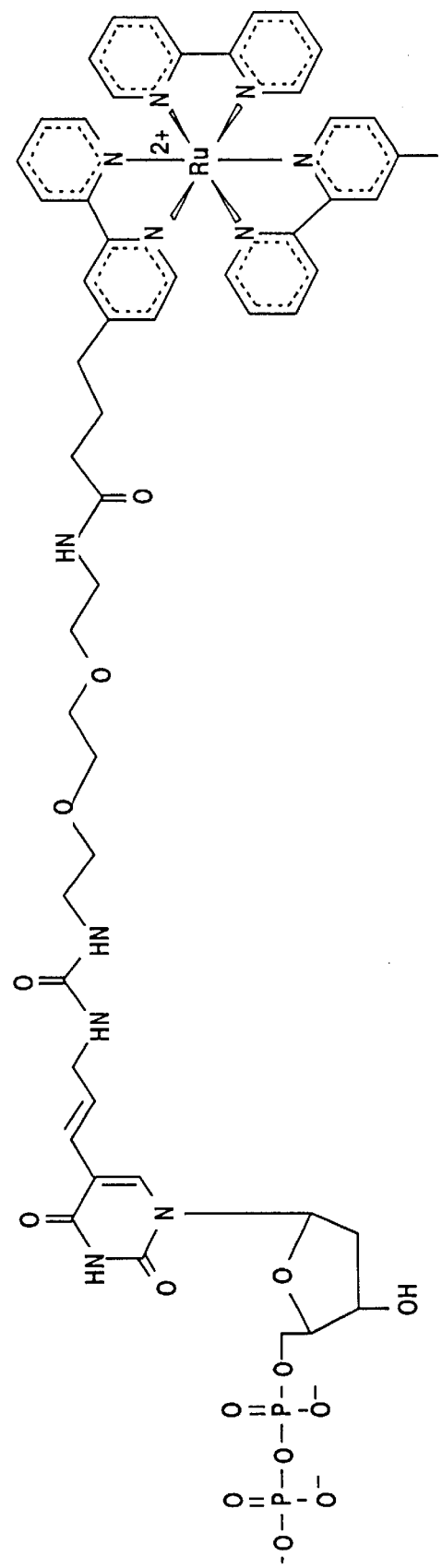
FIG. 8 shows the structure of Ru(bpyr)$_3$-DADOO-dUTP.

Synthesis of Ru(bpyr)$_3$-DADOO-dUTP (FIG. 8)

a. Synthesis of N-allyl-N'-(8-amino-3,5-dioxaoctyl)urea 15 g (0.1 mol) diaminodioxaoctane (Merck) were cooled to −40° C. in 500 ml diisopropylether. 5.5 g (0.06 mol) allylisocyanate (Fluka) were added slowly and dropwise. After stirring for 30 min. at −40° C., the mixture was allowed to reach RT and the diisopropylether was removed by distillation. The remainder was stirred for 1 h with 600 ml acetic ester, the precipitate was removed by filtration and washed three times with acetic ester. The combined acetic ester fractions were concentrated and the resulting product was purified by means of flash chromatography with an acetic ester/methanol solvent gradient of 9:1 to 8:2.

Yield: 4.5 g (29% of theoretical) colorless liquid.

b. Reaction with 5-mercury-dUTP 5-mercury-dUTP (=HgdUTP) was prepared according to Bergstrom et al. (1977). *J. Carbohydr., Nucleosides, Nucleotides* 4:257.

370 mg (0.54 mmol) HgdUTP and 113 mg K$_2$PdCl$_4$ are dissolved in 20 ml sodium acetate buffer (pH 5). Then, 0.5 g (2.16 mmol) N-allyl-N'-(8-amino-3,5-dioxaoctyl)urea were added dropwise and stirred overnight at RT. The precipitate is removed by filtration, the filtrate is concentrated and purified by means of ion exchange chromatography (DEAE-Sephadex-CL-Form) with a buffer gradient of 0 to 0.3 M LiCl. Subsequently, the product is precipitated twice form aceton/ethanol=2:1; the precipitate is removed by filtration, washed and dried. The result is 60 mg DADOO-dUTP (15.7% of theoretical).

c. The synthesis was carried out as described for Ru(bpyr) 3-AA-dUTP by reacting DADOO-dUTP with the Origen® label.

EXAMPLE 6

PCR Amplification and Labelling of HBV-DNA with Ru(bpyr)$_3$-AA-dUTP and Ru(bpyr)$_3$-DADOO-dUTP Portions of 1 ng Hpbadw21 were amplified; the volume of the PCR reaction mixture was 100 μl (80 μl PCR Mix, 20 μl sample).

The PCR Mix had the following composition:

| Reagent or sample | Concentration of stock-solution | Final concentration in the PCR |
|---|---|---|
| Hpbadw211 | | ng/100 μl |
| Primer 1 | 5 μM | 200 nM |
| Primer 2 | 5 μM | 200 nM |
| dATP (Li-Salt) | 4 mM | 200 μM |
| dCTP (Li-Salt) | 4 mM | 200 μM |
| dGTP (Li-Salt) | 4 mM | 200 μM |
| dTTP (Li-Salt) | 4 mM | 133 μM–200 μM |
| Ru(bpyr)3-AA-dUTP or | 700 μM | 66 μM–0.01 μM |
| RU(bpyr)3-DADOO-dUTP | 300 μM | 66 μM—0.01 μM |
| PCR-Puffer | 10 x | 1 x |
| Taq-Polymerase | 5 U/μl | 2.5 U |

10 x PCR-Puffer: 100 mM Tris/HCl, 500 mM KCl, 15 mM MgCl$_2$, 100 mg/ml gelatine, pH 9.0
Primer 1: oligodeoxynucleotide, 18 mer, d (GGAGTGTGGATTCGCACT) SEQ. ID. NO. 1 (Pos. 2267–2284; EMBL. subtype adw)
Primer 2: oligodeoxynucleotide, 18 mer d (TGAGATCTTCTGCGACGC) SEQ. ID. NO. 2 (Pos. 2436c–2419c; EMBL; subtype adw)
Hpbadw 21: adw 21 cloned in pUC BM 20 (Boehringer Mannheim) and linearized The PCR reaction mixtures were amplified in a Perkin Elmer Thermal Cycler with 30 cycles of 60 sec at 94° C., 60 sec at 50° C., and 120 sec at 70° C.

The Ru(bpyr)$_3$-AA-dUTP and Ru(bpyr)$_3$-DADOO-dUTP concentrations varied between 66 μM, 30 μM, 10 μM, 1 μM, and 0.1 μM to 0.01 μM, the dTTP concentrations were increased correspondingly to have a total Ru(bpyr)$_3$-dUTP/ dTTP concentration of 200 μM in the amplification mixture.

To have a comparison, the same PCR reaction mixture was tested where different concentrations of digoxigenin-11-dUTP (Boehringer Mannheim, Cat. No. 1039 088) were incorporated and also a PCR reaction mixture where no modified nucleotides were incorporated.

| No. | dTTP $\mu$M | Ru(bpyr)3 dUTP (short) $\mu$M | No. | dTTP $\mu$M | Ru(bpyr)3 dUTP (long) $\mu$M | No. | dTTP $\mu$M | DigdUTP $\mu$M | No. | DTTP $\mu$M |
|---|---|---|---|---|---|---|---|---|---|---|
| 1 | 133 | 66 | 1/1 | 133 | 66 | 1/2 | 133 | 66 | 1/3 | 133 |
| 2 | 170 | 30 | 2/1 | 170 | 30 | 2/2 | 170 | 30 | 2/3 | 170 |
| 3 | 190 | 10 | 3/1 | 190 | 10 | 3/2 | 190 | 10 | 3/3 | 190 |
| 4 | 199 | 1 | 4/1 | 199 | 1 | 4/2 | 199 | 1 | 4/3 | 200 |
| 5 | 200 | 0.1 | 5/1 | 200 | 0.1 | 5/2 | 200 | 0.1 | | |
| 6 | 200 | 0.01 | 6/1 | 200 | 0.01 | 6/2 | 200 | 0.01 | | |

| Lane | Mixture No. | Lane | Mixture No. | Lane | Mixture No. |
|---|---|---|---|---|---|
| I | 1 | IX | 3 | XVI | 4/3 |
| II | 1/1 | X | 3/1 | XVII | 5 |
| III | 1/2 | XI | 3/2 | XVIII | 5/1 |
| IV | 1/3 | XII | 3/3 | IXX | 5/2 |
| V | 2 | XIII | 4 | XX | 6 |
| VI | 2/1 | XIV | 4/1 | XXI | 6/1 |
| VII | 2/2 | XV | 4/2 | XXII | 6/2 |
| VIII | 2/3 | | | | |

Figure 9A:
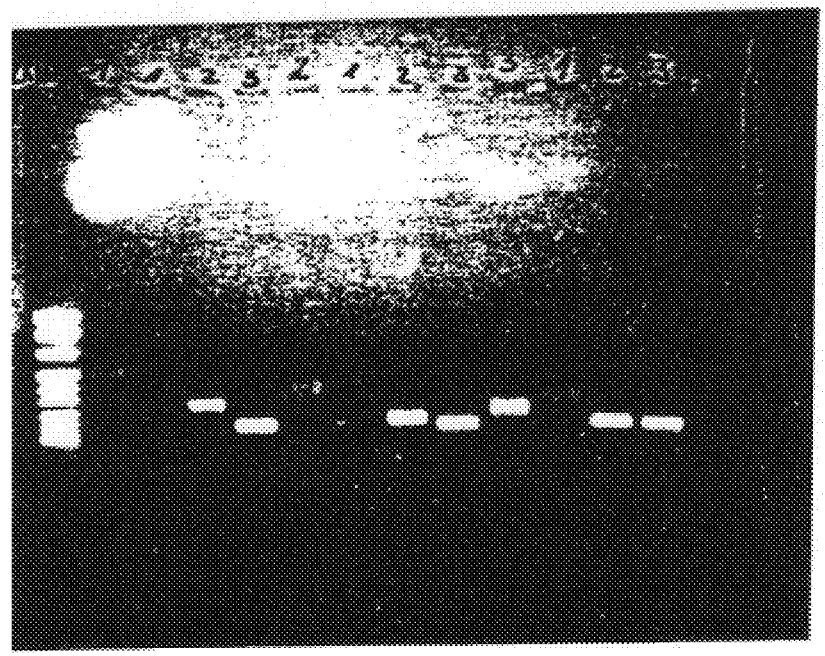
FIG. 9 is picture of an agarose gel showing the differences in the molecular weight of the labelled nucleic acid.
Figure 9B:
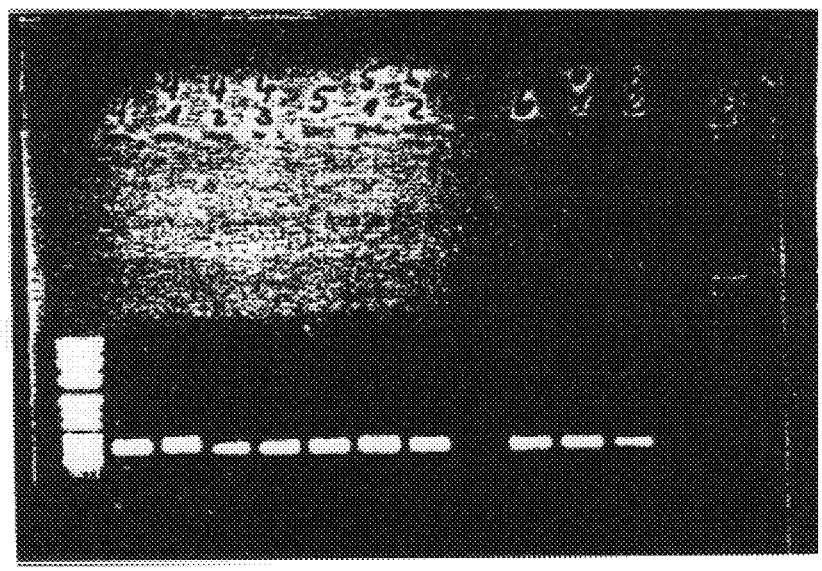

The different PCR reaction mixtures were applied onto a 1% agarose gel in portions of 10 $\mu$l and the amplification products were made visible by ethidium bromide (FIG. 9). Owing to its higher molecular weight, the amplification product with incorporated Ru(bpyr)$_3$-DADOO-dUTP (=long spacer) is more retarded on the gel than the Ru(bpyr)$_3$-AA-dUTP product (=short spacer). This, however, occurs only when higher concentrations of modified nucleotide are present and thus a correspondingly larger amount of label is incorporated during the amplification reaction. The result is an increase in the molecular weight as compared to the unmodified product.

EXAMPLE 7

Filter Hybridization with a Biotinylated Oligonucleotide Probe

Biotinylated capture probe:

d(AGA CCA CCA AAT GCC CCT AT) SEQ. ID. NO. 11 biotinylated with biotinamidite (Applied Biosystems) corresponds to Pos. 2297–2316 of the HBV$_{adw}$-sequence; EMBL sequence data bank. Ref: Ono et al. (1983). Nucl. Acids Res. 11:1747–1757.

Figure 10:
FIG. 10 shows the detection of amplification products with different amounts of either (bpyr)$_3$ AA dUTP or Ru(bpyr)$_3$-DADOO-dUTP incorporated by hybridization with a Biotin-labelled probe in the gel.

10 $\mu$l of the PCR reaction mixtures 1–6, 1/1–6/1 and 1/3–2/3 were applied onto a 1% agarose gel, then blotted onto a nylon membrane and hybridized at 45° C. overnight with portions of 100 ng of the above described biotinylated oligonucleotide probe corresponding to C. H. Kessler et al. (1980) "Non-radioactive labelling and detection of nucleic acids", Biol. Chem. Hoppe-Seyler 371:917–927. Biotin was detected with a conjugate consisting of streptavidin and alkaline phosphatase (Boehringer Mannheim, Cat. No. 1093 266), NBT/X-phosphate (Boehringer Mannheim, Cat. No. 1383 213 and 760 986). As shown in FIG. 10, the desired amplification product could be detected in all PCR reaction mixtures by means of hybridization using an oligonucleotide probe specific for the amplification product.

EXAMPLE 8

Hybridization and Detection 8.1 "Two-step assay"

10 $\mu$l of the mixtures 1, 4, and 6 as well as 1/1, 4/1, and 6/1 were diluted 1:10 with 0.05 M NaOH. After 5 min, 100 $\mu$l of this mixture were then neutralized with 500 $\mu$l of hybridization buffer 62.5 mM Na-phosphate, 0.94 M NaCl, 94 mM Na-citrate, pH=6.5) which already contained the biotinylated oligonucleotide probe in a concentration of 94 ng/ml. At the same time, the PCR reaction mixtures 1, 4, and 6 as well as 1/1, 4/1 and 6/1 were subjected to thermal denaturing by heating them up to 100° C., and subsequent cooling on ice. After hybridizing for 1 hour at 375° C., 50 $\mu$l of a suspension of streptavidin-coated magnetic particles (Dynabeads® M-280, streptavidin, Dynal) in hybridization buffer (concentration 600 $\mu$g/ml) were added and incubated for another hour at 37° C. Using a magnet, the magnetic beads were then collected on the bottom of the sample cup and the supernatant solution was decanted and the beads were again washed twice, each time with 500 $\mu$l phosphate buffer (50 mM Na-phosphate buffer; pH=7.4). Finally, the beads were suspended in 200 $\mu$l phosphate buffer, then 500 $\mu$l ECL assay buffer were added (see Blackburn et al. (1991). Clin. Chem. 37:1534–1539 and measured on an ECL analyzer (Origen® 1.0, IGEN, Rockville, USA).

The measurement was carried out with a photomultiplier voltage of 940 V. The measurement time was 2 sec. at a ramp voltage of 2 V per second. The complete measuring cycle for each sample was 2 minutes.

8.2 "One-step assay"

In this second and more simple assay procedure, denaturing of the PCR reaction mixture and hybridization with the biotinylated capture probe were carried out as described for the two-step-assay. After 2 hours of hybridization at 37° C. another 50 $\mu$l of magnetic bead were pipetted into this solution and then directly measured in the ECL analyzer without "bound/free" separation. The blank measured was the corresponding concentration of Ru(bpyr)$_3$-AA-dUTP in the hybridization buffer.

The voltage of photomultiplier was 800 V, all other measurement conditions corresponded to those described above.

Figure 11:
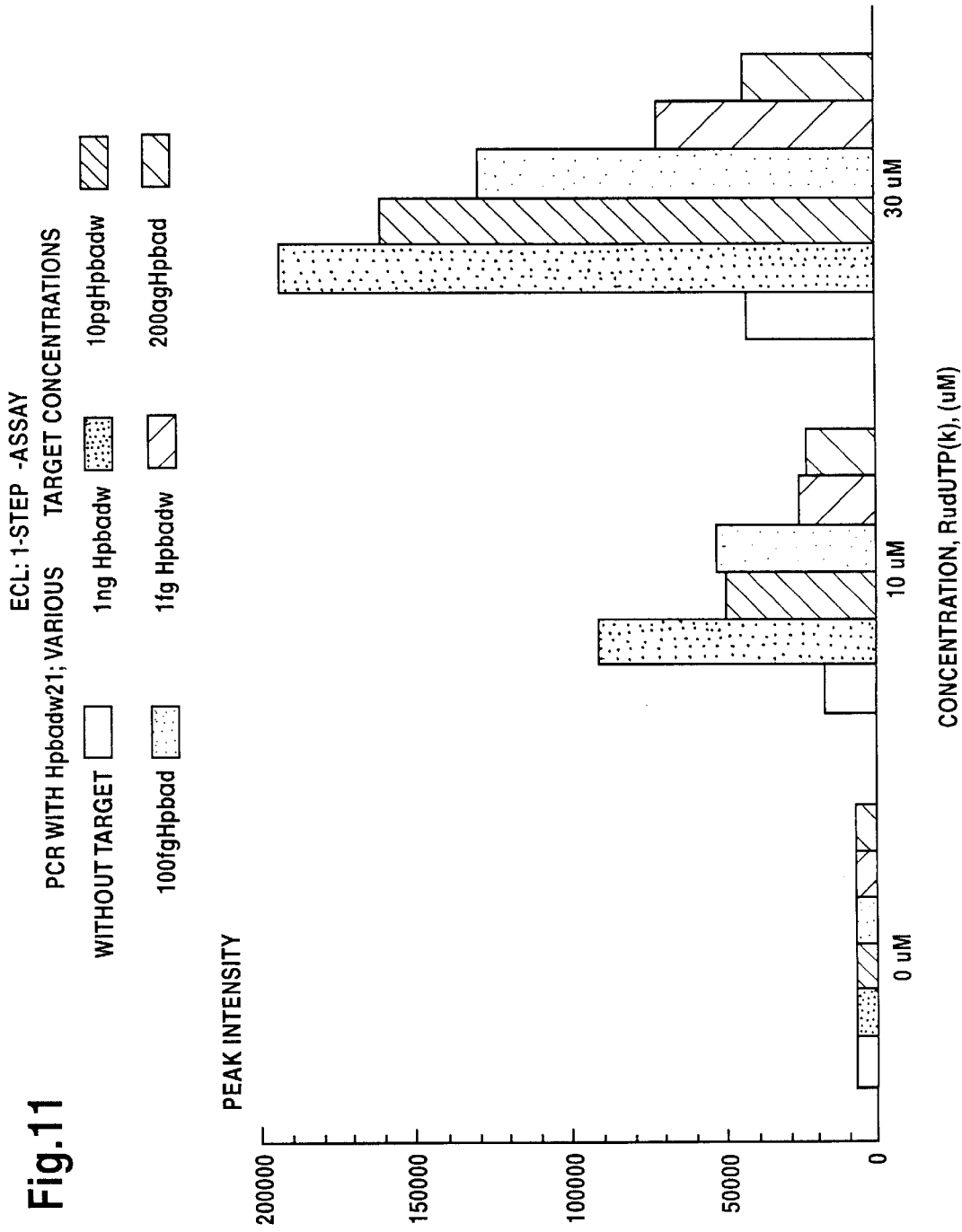
FIG. 11 is a graph showing the dependencies of the signal height upon the amount of ruthenium-labelled mononucleotides used in the reaction.

FIG. 11 also shows the ECL peak intensities measured in dependency on different Ru(bpyr)$_3$-AA-dUTP and Ru(bpyr)$_3$-DADOO-dUTP concentrations in the amplification mixture.

EXAMPLE 9

Detection of HBV Plasmid-DNA

The target was again Hpbadw 21. It was used with the following concentrations: 1 ng, 1 pg, 100 fg, 1 fg, 200 ag.

Amplification was carried out corresponding to the conditions of example 2: once using 10 μM (Ru(bpyr)$_3$-AA-dUTP/190 μl dTTP and once using 30 μM Ru(bpyr)$_3$-AAdUTP/170 μl dTTP final concentration in the PCR. Following hybridization with the biotinylated capture probe (Seq. Id. No. 3) and binding to SA magnetic beads according to the "one-step-assay" without "bound/free" separation, the amplification product was measured in the Origen® 1.0 Analyzer. The photomultiplier voltage used was 900 V, all other conditions corresponded to those described under item 4.2.

Figure 12:
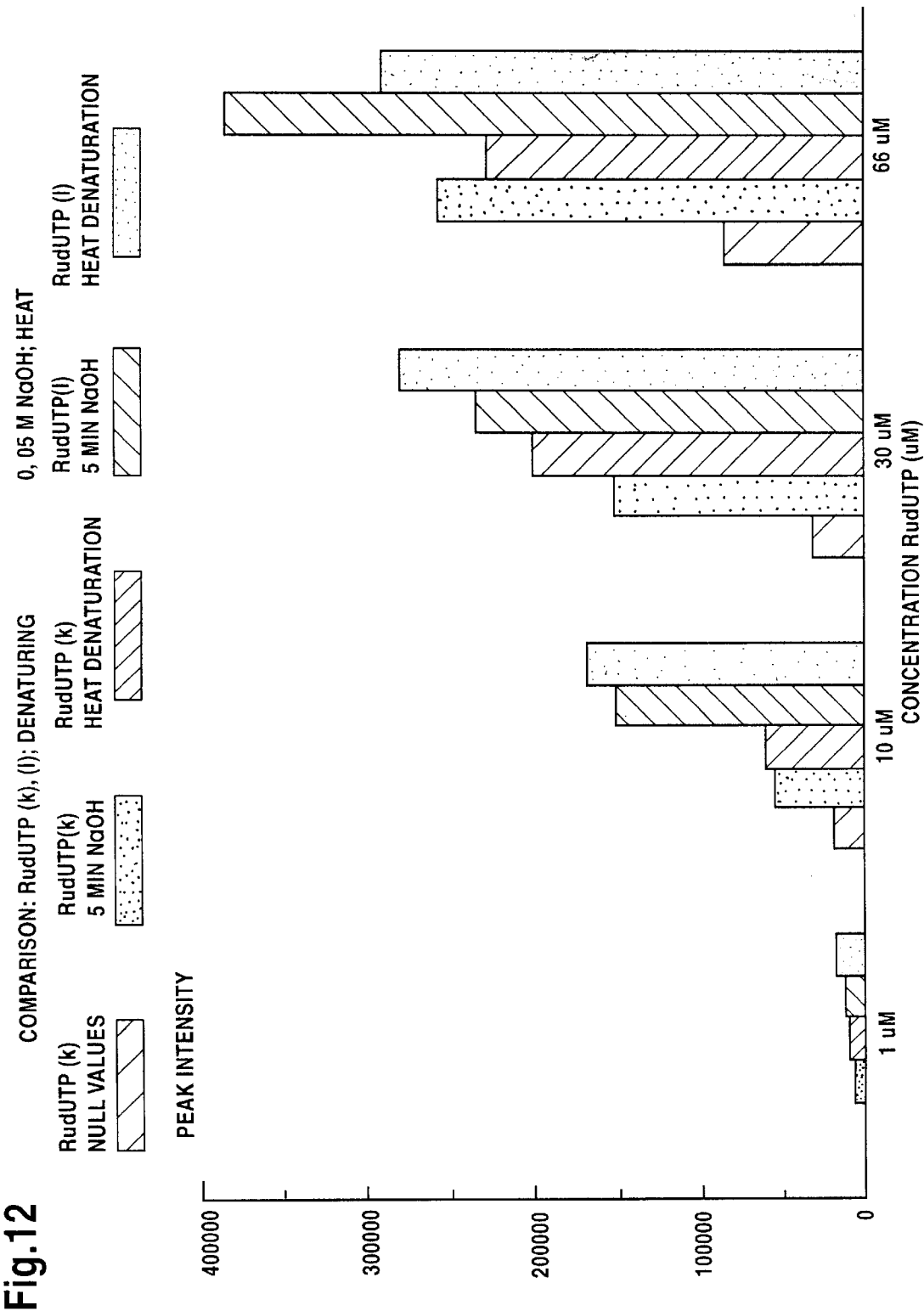
FIG. 12 is another graph showing the quantity-dependent detection of nucleic acid when ruthenium labels are incorporated.

FIG. 12 shows the measured ECL peak intensities in dependency on the different target concentrations.

EXAMPLE 10

Detection of HBV Using the Probe Directly During Thre PCR in Microtiterplates Coated with Thermostable SA The PCR mixture was prepared as described in Example 1. However, the volume of the mixture was reduced to 50 μl and covered with 30 μl Sigma mineral oil (Sigma Mineral Oil, light white oil M-3516. The primers, the biotinylated capture probe II, and the template as well as the concentrations used were identical. The PCR was carried out in Techne plates (Cat. No. 140800) coated with thermostable streptavidin (SA) prior to starting the procedure. A MW-2 Techne-Cycler was used for the amplification. The cycle conditions were the same as those used in example 1. After the PCR, the mixture was allowed to stand for 30 min at 37° C. Then it was washed three times (see example 1) and the plate was incubated with 100 μl conjugate buffer (see Example 1) and the plate was incubated with 100 μl conjugate buffer (see Example 1) for each well. Subsequently it was washed again three times and then reacted with 100 ml ABTS® solution (see Example 1). The absorbance measured is shown in FIG. 13. The bars on the right side (SA-MTP PCR) show the absorbances for the various concentrations.

EXAMPLE 11

Detection of HBV Using the Probe Directly During Thre PCR in Microtiterplates Coated with Thermostable SA The vessels used were 0.5 ml Perkin Elmer cups (Cat. No.: N801.0537 for the PCR Cycler 9600. The insides of the cups were coated with thermostable streptavidin according to EP-B-0 331 127. The reaction mixture was prepared as in Example 10. However, the volume of the reaction mixture was 100 μl and the PCR was not covered with oil. Conjugate buffer and ABTS® were added to the cups in portions of 200 μl/cup. After incubating with ABTS® for 15 min, the mixture was transferred into a Nunc plate (Cat. No.: 838713) and measured in the reader. The absorbances measured are given in FIG. 13 (center bars).

EXAMPLE 12

Coating the Techne Plates and the EP-Cups with Thermostable Streptavidin

The coating was carried out according to EP-B-0 331 127.

---

We claim:

1. A mononucleoside triphosphate having the formula I:

P-Z-B-E    (I)

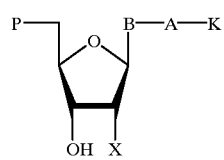

or alkali and earth alkali salts thereof, wherein

P is a triphosphate group or a triphosphate analog group,

Z is a sugar or sugar analog group,

B is a nucleobase analog group, and

E is an electrochemiluminescence group.

2. The triphosphate according to claim 1, wherein said triphosphate has the structural formula Ia:

wherein

X is hydrogen or $OR^1$, $R^1$ is selected from the group consisting of $C_1$–$C_6$ alkyl group, a $C_1$–$C_6$ alkylene group and hydrogen, B is selected from the group consisting of a purine, deazapurine and a pyrimidine group, A is a spacer group, and K is an electrochemiluminescent coordination complex.

3. The triphosphate according to claim 1, wherein the electrochemiluminescence group is a coordination complex of a metal ion and at least one organic ligand having an atomic weight greater than 500 g/mol.

4. The triphosphate according to claim 1, wherein the molecular weight of E is between 550 and 2000 g/mol.

5. A method for the extension of an oligonucleotide comprising the steps of:

hybridizing an oligonucleotide to a first nucleic acid, and extending said oligonucleotide by a mononucleoside triphosphate having the formula I

P-Z-B-A-K  (I)

at the 3'-end of said oligonucleotide using a polymerase, wherein

P is a triphosphate group or a triphosphate analog group,

Z is a sugar or a sugar analog group,

B is a nucleobase or a nucleobase analog group, and

K is an electrochemiluminescent coordination complex, and

A is a spacer group, wherein the molecular weight of K is between 550 and 2000 g/mol.

6. The method according to claim 5, wherein said triphosphate has the structural formula Ia:

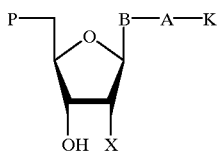

or alkali and earth salts thereof,
wherein

X is hydrogen or OR$^1$,

R$^1$ is selected from the group consisting of a C$_1$–C$_6$ alkyl group, a C$_1$–C$_6$ alkylene group and hydrogen, B is selected from the group consisting of a purine, deazapurine and a pyrimidine group, A is a spacer group, and K is an electrochemiluminescent coordination complex.

7. A method for the determination of a nucleic acid comprising the steps of hybridizing a primer to the nucleic acid to be determined, extending the 3'-end of said primer by attaching a mononucleoside triphosphate having the formula I:

P-Z-B-A-K  (I)

wherein

P is a triphosphate group or a triphosphate analog group,

Z is a sugar or a sugar analog group,

B is a nucleobase or a nucleobase analog group,

K is an electrochemiluminescent coordination complex, and

A is a spacer group, using a polymerase, to produce an extension product and determining any electrochemiluminescence group in the extension product as a measure of the nucleic acid to be determined.

8. The method according to claim 7, wherein the extension reaction is performed in a cyclic manner.

9. The method according to claim 7, wherein said triphosphate has the structural formula Ia:

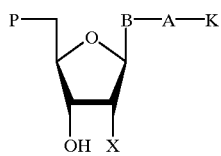

or alkali and earth salts thereof,
wherein

X is hydrogen or OR$^1$,

R$^1$ is selected from the group consisting of a C$_1$–C$_6$ alkyl group, a C$_1$–C$_6$ alkylene group and hydrogen, B is selected from the group consisting of a purine, deazapurine and a pyrimidine group, A is a spacer group, and K is an electrochemiluminescent coordination complex.

* * * * *

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

GGAGTGTGGA TTCGCACT                              18

(2) INFORMATION FOR SEQ ID NO:2:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:2:

TGAGATCTTC TGCGACGC                              18

(2) INFORMATION FOR SEQ ID NO:3:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
AGCCTATAGA CCACCAAATG CCCCTAT                                            27
```

(2) INFORMATION FOR SEQ ID NO:4:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

```
AATTCTAATA CGACTCACTA TAGGGAGACG CGCTTTACCT GCTTCGGCGA TT               52
```

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

```
GTAATCATCC GAAACCGCTC A                                                  21
```

(2) INFORMATION FOR SEQ ID NO:6:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

```
CGTTTTACTT CTTGGACCG                                                     19
```

(2) INFORMATION FOR SEQ ID NO:7:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:7:

```
CGUUUUACUU CUUGGACCG                                                     19
```

(2) INFORMATION FOR SEQ ID NO:8:

(i) SEQUENCE CHARACTERISTICS:
        (A) LENGTH: 47 base pairs

```
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:8:

AATTCTAATA CGACTCACTA TAGGGCCTGG CTTTAATTTT ACTGGTA                47

(2) INFORMATION FOR SEQ ID NO:9:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:9:

ACAGGAGCAG ATGATACAGT ATTAG                                       25

(2) INFORMATION FOR SEQ ID NO:10:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: RNA (xi) SEQUENCE DESCRIPTION: SEQ ID NO:10:

UGGAAGAAAU CGUUGACUC AGAUUGGUUG C                                 31

(2) INFORMATION FOR SEQ ID NO:11:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:11:

AGACCACCAA ATGCCCCTAT                                             20
```